(12) United States Patent
Mizoguchi et al.

(10) Patent No.: US 7,846,976 B2
(45) Date of Patent: Dec. 7, 2010

(54) METALLIC FINE PARTICLES, PROCESS FOR PRODUCING THE SAME, COMPOSITION CONTAINING THE SAME, AND USE THEREOF

(75) Inventors: Daigou Mizoguchi, Hitachinaka (JP); Yoshiaki Takata, Naka-gun (JP); Jun-etsu Satoh, Akita (JP); Hiroki Hirata, Saitama (JP); Masato Murouchi, Otawara (JP)

(73) Assignees: Mitsubishi Materials Corporation, Tokyo (JP); Dai Nippon Toryo Co., Ltd., Osaka (JP)

( * ) Notice: Subject to any disclaimer, the term of this patent is extended or adjusted under 35 U.S.C. 154(b) by 586 days.

(21) Appl. No.: 11/721,108

(22) PCT Filed: Dec. 8, 2005

(86) PCT No.: PCT/JP2005/022556

§ 371 (c)(1),
(2), (4) Date: Jun. 7, 2007

(87) PCT Pub. No.: WO2006/062160

PCT Pub. Date: Jun. 15, 2006

(65) Prior Publication Data

US 2009/0283726 A1 Nov. 19, 2009

(30) Foreign Application Priority Data

Dec. 10, 2004 (JP) ............... 2004-359190

(51) Int. Cl.
*C09K 3/00* (2006.01)
(52) U.S. Cl. ............... 516/97; 75/343; 252/582; 428/401; 428/403
(58) Field of Classification Search ............... 516/97; 252/582; 75/343; 428/401, 403
See application file for complete search history.

(56) References Cited

U.S. PATENT DOCUMENTS 4,294,609 A 10/1981 Taricco et al.

6,696,237 B1 * 2/2004 Yoshioka et al. ............ 430/619

FOREIGN PATENT DOCUMENTS

| EP | 1769867 A1 | 4/2007 |
| JP | 2-294414 A | 12/1990 |
| JP | 04-116109 | * 4/1992 |
| JP | 4-116109 A | 4/1992 |
| JP | 11-080647 A | 3/1999 |
| JP | 2001-064794 A | 3/2001 |
| JP | 2001-181713 A | 7/2001 |
| JP | 2004-024006 | * 4/2005 |
| JP | 2005-097718 | * 4/2005 |
| TW | 196193 | 12/1992 |
| TW | 200406272 | 5/2004 |

OTHER PUBLICATIONS

An Improved Synthesis of High-Aspect-Ratio Gold Nanorods, Adv. Mater., 15, No. 5, Mar. 2003, p. 414-416.*
"Photochemical Synthesis of Gold Nanorods", Kim et al., American Chemical Society, 124, 2002, pp. 14316-14317.
"Gold Nanorods: Electrochemical Synthesis and Optical Properties" by Yu et al., The Journal of Physical Chemistry B., vol. 101, No. 34, Aug. 21, 1997, pp. 6661-6663.
"Seed-Mediated Growth Approach for Shape-Controller Synthesis of Spheroidal and Rod-like Gold Nanoparticles Using a Surfactant Template**" by Jana et al., Adv. Mater. 2001, 13, No. 18, Sep. 14, pp. 1389-1393.
N. R. Jana et al., Wet Chemical Synthesis of High Aspect of Ratio Cylindrical Gold Nanorods, Journal of Physical Chemistry. B., vol. 105, No. 19, May 2001, pp. 4065-4067.

* cited by examiner

*Primary Examiner*—Ling-Siu Choi
*Assistant Examiner*—Chun-Cheng Wang
(74) *Attorney, Agent, or Firm*—Leason Ellis LLP.

(57) ABSTRACT

A process for producing metallic fine particles is provided by, the reduction of the metallic ions performed in two steps using two types of reducing agents which significantly differ in reducing ability thereof, in which a reducing agent in which the reduction ability is strong is used in the first reduction step, and a reducing agent in which the reduction ability is weak is used in the second reduction step, and the nano-sized metallic fine particles are produced. An aqueous metallic salt solution containing a surfactant is used and a two-step reduction is performed in the same vessel, in which as the reducing agent of the first reduction process, at least one selected from the group consisting of boron hydride, dimethylamine borane, hydrazine, and ascorbic acid is used, and as the reducing agent of the second reduction process, specific alkylamine or alkanolamine is used.

7 Claims, 2 Drawing Sheets

METALLIC FINE PARTICLES, PROCESS FOR PRODUCING THE SAME, COMPOSITION CONTAINING THE SAME, AND USE THEREOF

CROSS REFERENCE TO RELATED APPLICATIONS

This is a U.S. national phase application under 35 U.S.C. §371 of International Patent Application No. PCT/JP2005/022556, filed Dec. 8, 2005, and claims the benefit of Japanese Patent Application No. 2004-359190, filed Dec. 10, 2004, both of which are incorporated by reference herein. The International Application was published in Japanese on Jun. 15, 2006 as International Publication No. WO 2006/062160 under PCT Article 21(2).

TECHNICAL FIELD

The present invention relates to a process for producing metallic fine particles having a superior reproducibility in terms of particle size and light absorption characteristics, the metallic fine particles, a composition containing the particles, and the use thereof.

BACKGROUND ART

As methods of combining metallic fine particles, an electrochemical method (Y.-Y. Yu, S.-S. Chang, C.-L. Lee, C. R. C. Wang, J., Phys. Chem. B, 101, 6661 (1997) ), a chemical method (N. R. Jana, L. Gearheart, C. J. Murphy, Adv. Mater. Vol. 13, No. 18, 1389 (2001)), and a photochemical method (E Kim, J. H. Song, P. Yang, J. Am. Chem. Soc., 124, 14316 (2002)) are known in the art. In addition, as a method of producing spherical noble metal particles as coating material or coloring material of resin composition, a method of dissolving noble metal in solvent, adding a high-molecular weight compound thereto and then resolving the resultant solution is known in the art (Japanese Unexamined Patent Publication No. 11-80647). Furthermore, Japanese Unexamined Patent Publication No. 2001-64794 discloses the formation of metallic wiring patterns, using fine rods in which inorganic particulates are supported on a solid surface and absorbing Plasmon. These wiring patterns grew to a diameter of less than 100 nm and an aspect ratio of not less than 1 was obtained.

The electrochemical method is to resolve metallic ions dissolved from an anode and then grow the resolved metallic ions into rod-like fine particles by the action of a surfactant under ultrasonic irradiation. The electrochemical method requires an electrolytic apparatus, expensive conducting electrodes such as gold plates, platinum plates or silver plates, and ultrasonic irradiation, and also the obtainable amount is limited according to the size of the apparatus. Therefore, this method is unsuitable for large-scale production. Moreover, because the aspect ratio of the metal nano rods depends on the degradation of the ultrasonic transmitter or the dissolved amount of silver, the reproducibility is not uniform.

A known chemical method is to add a reducing agent to a metallic salt to initially create fine metallic species as a growing core, add a predetermined amount of solution including these metallic species to a growth solution contained in a separate vessel, and then grow rods having a rod-like structure. When the initially produced metallic species have a short working life and the growth solution contains any reducing agents, both the first reducing agent and the second reducing agent have a strong reduction ability. Hence, the growth of the metallic fine particles progresses nonuniformly and thereby metallic fine particles having low reproducibility are obtained. Further, this method produces metallic nanorods have a low concentration.

The photochemical method is to irradiate the metallic ions included in a surfactant-containing solution for long time and then produce metal nanorods. The method requires expensive apparatuses such as an ultraviolet exposure apparatus, and also the obtainable product is limited by the range of light irradiation. As a result, the yield is limited, and therefore the method is unsuitable for large-scale production.

For the production process of Japanese Unexamined Patent Publication No. 11-80647, an example employing amine as the reducing agent is disclosed. According to the disclosed method, by combining spherical noble metal particles with a high-molecular-weight pigment agent, rod-like metallic fine particles are not obtainable. Further, a high-molecular-weight dispersing agent is added to the raw material. However, the added dispersing agent is used as a protective colloid of the created noble metal particles. The dispersing agent does not grow the metallic fine particles into rods, and also no manner of employing the dispersing agent together with the reducing agent is known in the art. Furthermore, for the production process of Japanese Unexamined Patent Publication No. 2001-64794, the metallic fine particles are grown on a solid surface, and the metallic fine particles are supported on the solid surface. Therefore, the metallic fine particles can not be used separately, can not be dispersed in the various solvents, binders, and the thus obtained metallic fine particles can not be used as a composition for a coating material, etc.

In view of the above, it is an object of the present invention to address the aforementioned problems in connection with the known method of producing metallic fine particles. According to an aspect of the present invention, there is provided a process for producing the metallic fine particles by chemically reducing metallic ions, wherein the metallic fine particles have a superior reproducibility of particle size and light absorption characteristics. Further, according to another aspect of the present invention, there is provided metallic fine particles obtained by the aforementioned production process, a metallic fine particle-containing composition, and the use thereof.

SUMMARY OF THE INVENTION

The present invention includes the following production processes.

(1) A process for producing nano-sized metallic fine particles by chemically reducing metallic ions, in which the reduction of the metallic ions is performed in two steps using two types of reducing agent which significantly differ in reducing ability thereof, a reducing agent of which the reduction ability is strong, referred to as "strong reducing agent", is used in the first reduction step, and a reducing agent of which the reduction ability is weak, referred to as "weak reducing agent", is used in the second reduction step.

(2) The process described in (1) above, in which in the first reduction process, the strong reducing agent is added to an aqueous metallic salt solution, and the reduction is performed until the amount of metal ions in the aqueous metallic salt solution is in the range of 50 to 1%, and subsequently, in the second reduction process, the weak reducing agent is added to an aqueous metallic salt solution, and the reduction is performed until the amount of metal ions in the aqueous metallic salt solution is substantially 0%.

(3) The process described in (1) or (2) above, in which an aqueous metallic salt solution containing a surfactant, and two reducing agents which significantly differ in reducing ability thereof, are used, metallic ions in an aqueous metallic solution are reduced by adding the strong reducing agent to the aqueous metallic salt solution and subsequently adding the weak reducing agent to the solution, in the same vessel, and thereby a nano-sized rod-like metallic fine particles, referred to as "metal nano rod", is produced.

(4) The process described in any one of (1) to (3) above, wherein as the strong reducing agent of the first reduction process, at least one selected from the group consisting of boron hydride, dimethylamine borane, hydrazine, and ascorbic acid is used, and wherein as the weak reducing agent of the second reduction process, at least one of alkylamine and alkanolamine is used, which is represented by the following formulas (1) to (4):

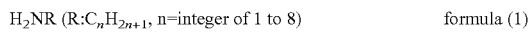
$$H_2NR \ (R:C_nH_{2n+1}, n=\text{integer of 1 to 8}) \quad \text{formula (1)}$$

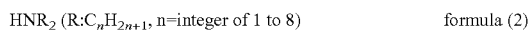
$$HNR_2 \ (R:C_nH_{2n+1}, n=\text{integer of 1 to 8}) \quad \text{formula (2)}$$

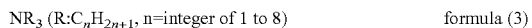
$$NR_3 \ (R:C_nH_{2n+1}, n=\text{integer of 1 to 8}) \quad \text{formula (3)}$$

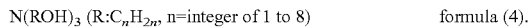
$$N(ROH)_3 \ (R:C_nH_{2n}, n=\text{integer of 1 to 8}) \quad \text{formula (4)}.$$

(5) The process described in (4) above, in which the concentration of amines represented by the formulas (1) to (4) present in the aqueous metallic salt solution is in the range of 0.0001 to 10 mol/L.

(6) The process described in any one of (3) to (5) above, in which the surfactant is an ammonium salt which substantially has no reducing ability and can be represented by the following formula (5):

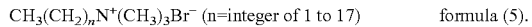
$$CH_3(CH_2)_nN^+(CH_3)_3Br^- \ (n=\text{integer of 1 to 17}) \quad \text{formula (5)}.$$

(7) The process described in any one of (3) to (6) above, in which the concentration of an ammonium salt represented by the formula (5) present in the aqueous metallic salt solution is in the range of 0.01 to 2.0 mol/L.

(8) The process described in any one of (1) to (7) above, in which the size of metallic fine particles is controlled by adjusting the additive amount of the strong reducing agent used in the first reduction process and the additive amount of the weak reducing agent used in the second reduction process.

In addition, the present invention relates to the following metallic fine particles and the use thereof.

(9) Rod-like metallic fine particles produced by the process described in any one of (1) to (8) above, wherein the particles have the length of the long axis of 400 nm or less, the length of the short axis of 30 nm or less, and the aspect ratio (the length of the long axis/the length of the short axis) of greater than 1.

(10) Metallic fine particles produced by the process described in any one of (1) to (8) above, which are surface-treated by a nonaqueous dispersing agent having side chains which have an affinity for a nonaqueous solvent other than water.

(11) Metallic fine particles produced by the process described in (1) or (2) above, in which the residual amount of the ammonium salt on the surface of metallic fine particles is not more than 15 parts by weight with respect to 100 parts by weight of the metallic fine particles.

(12) A composition containing any one of the metallic fine particles produced by the process described in any one of (1) to (8) above and the metallic fine particles produced by the process described in any one of (9) to (11) above.

(13) The composition described in (12) above, which further includes binders (resins) and dispersion media, together with the metallic fine particles.

(14) The composition described in (12) or (13) above, which further includes at least one of colorants, pigments, phosphors, metal oxides, and metal nanofibers, together with the metallic fine particles.

(15) A light absorbing material formed from the composition containing the metallic fine particles described in any one of (12) to (14) above, which is in any form of a coating material composition, a coat film, a film, and a plate.

(16) An optical filtering material, a wiring material, an electrode material, a catalyst, a coloring agent, a cosmetic, a near-infrared light absorber, an anticounterfeit ink, an electromagnetic shielding material, a surface-enhanced fluorescence sensor, a biological marker, a nano-waveguide, a recording material, a recording device, a polarization material, a drug container for a drug delivery system (DDS), a biosensor, a DNA chip, and a diagnostic agent, which include any one of the metallic fine particles produced by the process described in any one of (1) to (8) above and the metallic fine particles produced by the process described in any one of (9) to (11) above.

ADVANTAGES OF THE INVENTION

In view of the above, according to the present invention, there is provided a process of producing the metallic fine particles by chemically reducing metallic ions, wherein the reduction of the metallic ions is performed in 2 steps using two reducing agents which significantly differ in reducing ability thereof; a strong reducing agent is used in the first reduction step, a weak reducing agent is used in the second reducing agent step. As a result, most of the metallic ions are reduced in the first reduction process, and then all of the remaining metallic ions are reduced in the second reduction process. Simultaneously, the growth of the metallic fine particles proceeds and thereby the metallic fine particles having a uniform particles nano size can be obtained. The term "the metallic fine particles of the nano size" as used herein, represents the metallic fine particles in which the length of the axis is several hundred nano meters (nm).

Further, according to the production processes of the present invention, for example, the strong reducing agent is added to the aqueous metallic salt solution containing a surfactant in a vessel, and then the weak reducing agent is added to the same vessel. In other words, the metallic ions contained in the aqueous metallic salt solution are reduced. As a result, the rod-like metallic fine particles (metal nano rod) of the nano size can be produced. In particular, for example, large metal nano rods having the long axis of 400 nm or less, the short axis of 30 nm or less, and an aspect ratio (the length of the long axis/the length of the short axis) greater than 1 can be obtained. Further, by performing in 2 steps in the same vessel, the metallic fine particles can be effectively produced.

According to the production process of the present invention, since the reduction of the metallic ions is performed in 2 steps using two reducing agents which significantly differ in a reducing ability thereof, the metallic fine particles having good reproducibility can be obtained. Furthermore, since the added amount of the first reduction process and the added amount of the second reduction process is adjusted in the 2 steps, the particles diameter (aspect ratio) of the metallic fine particles can be controlled.

In the production process of the present invention, the appropriate surfactant used herein, is ammonium salt not substantially having reducing ability and which can be expressed as a following formula (5). By employing the aqueous metallic salt solution that ammonium salt is added to, the aqueous solution in which the metallic fine particles are stably dispersed can be obtained and also the metal nano rod can be effectively produced.

Since the metallic fine particles obtained by the production process of the present invention are subject to surface treatment by the nonaqueous dispersing agent including a side chain having affinity for the nonaqueous solvent (solvents other than water), a solution in which the metallic fine particles are preferably dispersed in the nonaqueous solvent can be obtained. Further, a solution in which the metallic fine particles are dispersed in the nonaqueous solvent may be used as the raw material of the metallic microparticle-containing composition. For example, the coating material composition containing binders (resin) and dispersion media, together with the metallic fine particles can be obtained.

In addition, the metal nano rod-containing composition of the present invention including colorants, pigments, phosphors, metal oxides, one or more of metal nano fibers, together with the metallic fine particles may be employed. The metallic fine particle-containing composition may be used in various forms, such as liquid of coating materials, coating films, films, or plates. In addition, the metallic fine particle-containing composition may be widely used in the materials of light absorbers or optical filters, wiring materials, electrode material, catalysts, coloring agents, cosmetics, near-infrared light absorbers, anticounterfeit inks, electromagnetic shielding materials, surface-enhanced fluorescence sensors, living body markers, nano waveguides, recording materials, recording devices, polarization materials, drug containers for drug delivery system (DDS), biosensor, DNA chips, test agents, etc.

DETAILED DESCRIPTION OF THE INVENTION

Figure 1:
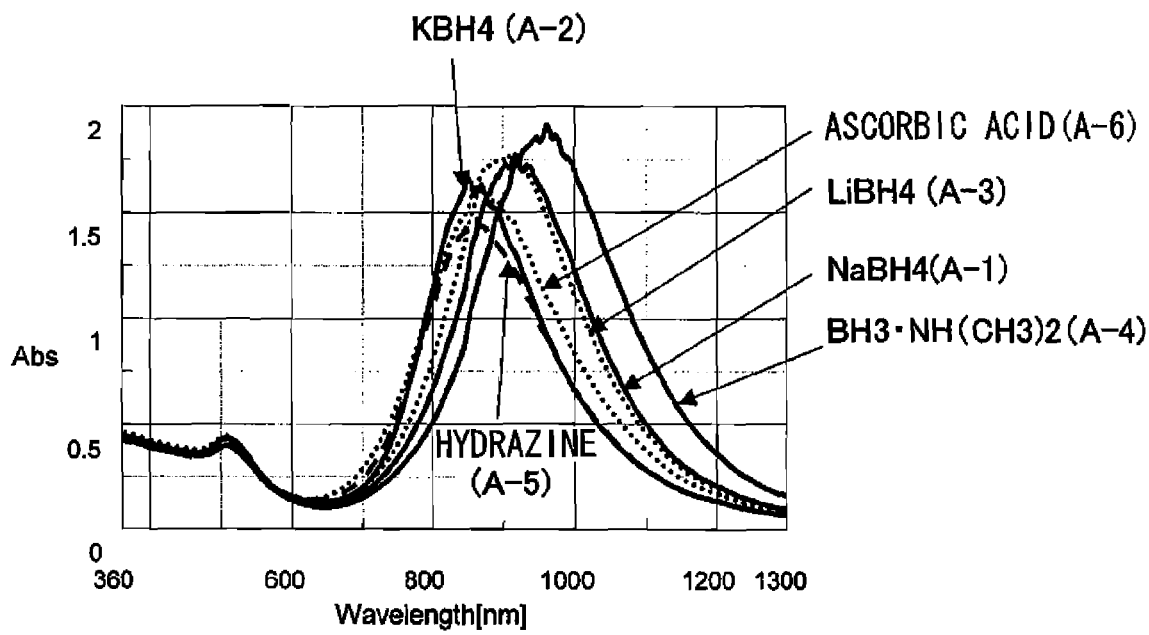
FIG. 1 is a graph illustrating dispersions of the Example A-1 to Example A-6.

An exemplary embodiment of the present invention will be described in greater detail with reference to the accompanying drawing hereinafter.

According to an aspect of the present invention, there is provided a process for producing metallic fine particles having nano-size by chemically reducing metallic ions, wherein the reduction of the metallic ions is performed in 2 steps using two reducing agents which significantly differ in reducing ability thereof; a strong reducing agent is used in the first reduction step, and a weak reducing agent is used in the second reducing agent step.

As used herein, the term "strong reducing agent" represents a reducing agent having a reduction ability such that 5 μmol of the reducing agent is added to 1 L of the aqueous solution containing 1 μmol of gold chloride acid and then it takes less than 30 minutes to precipitate the entire gold ions of the aqueous solution (the amount of the gold ions is zero) under the condition of room temperature (20° C.). On the other hand, the term "weak reducing agent" means a reducing agent that takes not less than 30 minutes to precipitate the entire gold ions of the aqueous solution (the amount of the gold ions is zero) under the same condition and the time difference with the strong reducing agent used in the first reduction process is not less than 10 minutes. By using the strong reducing agent and the weak reducing agent together, the metallic ions can be reduced uniformly, and thus the metallic fine particles having reproducibility of particle size can be obtained.

Chemical reduction of the metallic ions is performed by adding the reducing agent the aqueous solution to the aqueous metallic salt solution. Examples of such aqueous metallic salt solution include, but are not limited to, gold chloride acid aqueous solutions, silver nitrate aqueous solutions, copper nitrate aqueous solutions, etc. By chemically reducing these various metallic ions contained in the aqueous solution, nano-sized metallic fine particles can be produced.

In particular, for example, when combining the gold nano rod, the aqueous gold halide solution may be used. Gold concentration of the aqueous solution is preferably in the range of 10 to 4000 μmol/L in the aqueous solution, and more preferably in the range of 100 to 2500 μmol/L. If the gold concentration is less than the amount, production efficiency is decreased. On the other hand, if the gold concentration exceeds the amount, the uniform growth of the metallic fine particles is suppressed, and thus the reproducibility of the particle size is degraded.

Preferably, the aqueous metallic salt solution includes any one of the aqueous metallic salt solutions that the surfactant is added to. By adding the appropriate surfactant to the solution, agglomeration between the metallic fine particles is inhibited, and thus the aqueous solution in which the metallic fine particles are stably dispersed can be obtained. As the surfactant, the quaternary ammonium salt can be used, which can be expressed as the following formula (5):

$$CH_3(CH_2)_nN^+(CH_3)_3Br^- \qquad \text{formula (5)}$$

(n is an integer of 1 to 17)

The specific example of the quaternary ammonium salt includes, but is not limited to, hexadecyl trimethyl ammonium bromide (n=16, CT16AB). The quaternary ammonium salt is an aqueous cationic surfactant, and it is known that if it dissolves in water, the quaternary ammonium salt forms various aggregates (micelle) according to their concentrations. Generally, as the concentration of ammonium is increased, the quaternary ammonium salt is changed to spherical micelles, columnar micelles and plate-like micelles, in this order. By adjusting the concentration of the ammonium salt and also using the regularity of the micelles, rod production rate of the metallic fine particles can be increased compared to that of the spherical metallic fine particles.

The concentration of the quaternary ammonium salt in the aqueous metallic salt solution preferably is 10 mM to 2 M (0.01 to 2.0 mol/L), and more preferably 80 mM to 800 mM. If the concentration is too low, the dispersion stability of the metallic fine particles is decreased, and the created amount of the spherical fine particles is increased. On the other hand, if the concentration is too high, the viscosity of the aqueous metallic salt solution becomes large. Therefore, it is difficult to treat the quaternary ammonium salt and also it is disadvantageous to the production cost.

The metallic ions are reduced by adding the reducing agent to the aqueous metallic salt solution. The reduction of the metallic ions is performed in 2 steps using two reducing agents having a large difference between the reduction abilities; in the first reduction process the strong reducing agent is used, and the second reduction process the weak reducing agent is used. By using the strong reducing agent in the first reduction process, the reduction is performed until the amount of the metallic ions in the aqueous metallic salt solution is in the range of 50% to 1% in a short time, for example, for 30 minutes, and preferably the amount of the metallic ions becomes 40% to 5%. After terminating the first reduction process, if the amount of the metallic ions in the aqueous metallic salt solution is greater than 50%, the metallic ions can not be uniformly reduced in the second reduction process, and thus the reproducibility of the created particle size is degraded. On the other hand, if the amount of the metallic ions is less than 1% after the termination of the first reduction process, the growth of the metallic fine particles in the second reduction process progresses, and similarly the reproducibility of the particle size becomes worse. If the weak reducing agent is used in the first reduction process, it takes a long time to reduce and the metallic ions cannot be uniformly reduced. Hence, it is undesirable that the weak reducing agent be used in the first reduction process, because the reproducibility of the particle size becomes worse.

The strong reducing agent includes, for example, sodium boron hydride, dimethylamineborane, hydrazine, ascorbic acid, etc. Adding the strong reducing agent to the aqueous metallic salt solution is preferably completed by performing on several occasions, because the reduction becomes uniform and also the reproducibility of the particle size is improved. After the first reduction process, the second reduction process is performed by adding the weak reducing agent to the aqueous metallic salt solution.

The progress degree of reducing the metallic ions can be ascertained by measuring the metallic ions in the aqueous metallic salt solution using, for example, an inductively-coupled plasma spectrometer. Further, the aqueous metallic salt solution varies slowly in color, as the reduction progresses. Therefore, if the progress degree of the reduction and color at that time are ascertained in advance, even though the progress degree of the reduction is not measured at that time, the termination of the first reduction process and the time that the process proceeds to the second reduction process can be determined.

For example, if 200 μmol of sodium boron hydride is added to 1 L of an orange aqueous solution containing 1 mmol of gold chloride acid, since gold ions in the solution are reduced, the orange color of the aqueous solution becomes cloudy and then turns yellow (reduction rate of approximately 30%). Subsequently, if 200 μmol of sodium boron hydride is added to the resultant solution once again, the color of the added solution turns weak yellow (reduction rate of approximately 60%). Thereafter, if 200 μmol of sodium boron hydride is added to the resultant solution once again, the orange becomes cloudy or transparent (reduction rate of approximately 90%).

The additive amount of the strong reducing agent in the first reduction process is such an amount as to not completely reduce the metallic ions in the aqueous metallic salt solution, preferably is such an amount as to reduce the metallic ions until the amount of metallic ions in the aqueous metallic salt solution becomes 50% to 1%, and more preferably is such an amount as to reduce the metallic ions until the amount of the metallic ions becomes 40% to 5%. In particular, for example, in the reduction of the gold chloride acid, the additive amount of the strong reducing agent for 10 μmol of the gold chloride acid is 0.1 to 50 μmol, preferably 1 to 10 μmol.

If the reducing agent is excessively added to the solution, the metallic ions are rapidly reduced and then the spherical gold particles grow to the size having Plasmon absorption. As a result, even if the reducing agent of the second reduction process is added to the solution, the metallic ions in reaction solution are exhausted completely and thereby the growth to rod-like particles in the second reduction process occurs with difficulty. On the other hand, if the small amount of the reducing agent is added to the solution, the reduction of the metallic ions becomes inadequate and then in the second reduction process the growth of the particles becomes irregular, and thereby the reproducibility of the metallic fine particles becomes worse.

With respect to the N. R. Jana, L. Gearheart, C. J. Murphy, Adv. Mater. Vol. 13, No. 18, 1389 (2001), in the first reduction process by the sodium boron hydride, gold particles (Seed; seed particles) having the size of 3 to 4 nm are created (the solution turns into a red color by the wavelength absorption effect of the seed particles), the seed particles are added to a gold ion aqueous solution contained in a separate vessel in a fixed amount, and then gold nano rod is combined by performing the second reduction in the separate vessel. Unlikely, according to the combining process of the present invention, the reduction is performed using the sodium boron hydride in the first reduction process, whereas the first reduction process is terminated before the particles grow to the spherical particles having a size showing the Plasmon absorption and then in the second reduction process rod-like particles are obtained by reducing the remaining metallic ions in the reaction solution. Hence, according to the process, the high reproducibility of particle size or shape in the rod-like particles can be accomplished, and also high concentration of the metallic fine particles is obtainable.

Further, in the second reduction process, by using the weak reducing agent, the metallic ions having decreased valence of ion in the first reduction process are completely reduced, and then the created metal clusters grow to fine particles having desired shapes. The metallic ions in the solution at the time of terminating the first reduction process are reduced at least by half and then the valence of ions is decreased, and the metallic fine particles are created in such a small amount as to not produce the Plasmon absorption.

For example, in the reduction of gold chloride acid, since the gold ions are decreased by the first reduction process, the orange color of gold chloride acid aqueous solution becomes cloudy and then it becomes yellow aqueous solution or a transparent aqueous solution. If the second reduction is slowly performed by adding the weak reducing agent to the resultant aqueous solution, the reduction of gold ions is completed without producing rapid the growth of particles. In other words, since 100% of gold ions in the gold chloride acid aqueous solution are reduced, the subsequent growth of the particles can be controlled and also gold particles having a desired shape can be obtained.

The metallic fine particles have a wavelength absorption effect depending on the aspect ratio. Hence, as the metallic fine particles grow to rods in the solution, the color of the solution varies from transparent to a corresponding color to the absorption wavelength.

Preferably, the weak reducing agent is performed within 30 minutes after the strong reducing agent is added to the solution in the first reduction process. Metallic ions are reduced by the strong reducing agent within 30 minutes until the amount of the metallic ions in the aqueous metallic salt solution become 50% to 1%, subsequently the weak reducing agent of the second reduction process is added to the resultant solution. As a result, all remaining metallic ions are reduced, and thus the growth of the particles can be promoted.

The weak reducing agent used in the second reduction process includes, for example, alkyl amine or alkanolamine, which can be expressed as the following formulas (1) to (4):

$H_2NR$ ($R:C_nH_{2n+1}$, n=integer of 1 to 8)  formula (1)

$HNR_2$ ($R:C_nH_{2n+1}$, n=integer of 1 to 8)  formula (2)

$NR_3$ ($R:C_nH_{2n+1}$, n=integer of 1 to 8)  formula (3)

$N(ROH)_3$ ($R:C_nH_{2n}$, n=integer of 1 to 8)  formula (4)

By using the weak reduction ability of either the alkyl amine or the alkanol amine under the interfacial activity of the ammonium salt, a reaction field in which rod-like particles are slowly grown can be provided. The amine has properties such that hydrophobic property is stronger as the alkyl chain is longer and that it is not easy to dissolve in water. However, by using the amine together with the ammonium salt and also the emulsification of the ammonium salt, the amine can be mixed into the reaction aqueous solution.

If for example, the gold chloride acid aqueous solution is used as a raw material, the additive amount of the amine is approximately 0.0001 to approximately 10 mol/L in the reaction aqueous solution and preferably approximately 0.001 to approximately 1 mol/L. If the additive amount is greater than approximately 10 mol/L, the amine is not dissolved completely in the reaction aqueous solution containing the ammonium salt. Furthermore, the reduction reaction of the metallic ions occurs rapidly, and thus the created amount of the spherical particles is increased. On the other hand, if the additive amount is less than 0.0001 mol/L, the remaining metallic ions can not be completely reduced or the particles can not be grown. In addition, since it takes a long time to reduce the metallic ions, the reproducibility of the partice size becomes worse.

Of the amines, in particular, trialkylamine expressed as the formula (3) is preferred, because the creation of the spherical particles is suppressed and rod-like particles are created in the first place. Of these amines, trimethylamine, triethylamine, tripropylamine, tributhylamine, tripentylamine and trihexylamine are preferable, where n=1 to 6. If the length of the alkyl chain is greater, solubility to the reaction aqueous solution is decreased.

If the reducing agents such as sodium boron hydride, dimethylamineborane, hydrazine, ascorbic acid, etc., which have strong reduction and were used conventionally, are used as the reducing agent of the second reduction process, the metallic ions are rapidly reduced, the spherical metallic fine particles having relatively large diameter are produced, and rod-like particles can be hardly obtained. Further, if the reducing agent having a reduction ability weaker than that of the amines is used, the metallic ions can not be completely reduced or grown to particles; also it takes a long time to reduce the metallic ions, and thus the reproducibility of the partice size becomes worse.

The production process of the present invention controls the diameter of the metallic fine particles by adjusting the concentration and the kind of the surfactant, the amount and the kind of the strong reducing agent of the first reduction process, and the amount and the kind of the strong reducing agent of the second reduction process. Furthermore, according to the production process of the present invention, it allows obtaining particles in which the distribution of the particles diameter (for example, the length of the long axis or length of the short axis in the case of rod-like particles) is sharper than that of the known production process. Still further, it allows producing in the same vessel, the producing efficiency is high, and the reproducibility of the combination is high.

For example, by increasing the concentration of the surfactant, the viscosity of the aqueous metallic salt solution is increased, and reduction speed of the metallic ions or the growth speed of the metallic nanorods is slow. Hence, a rapid reaction occurs that is easy to grow to large particles and the creation of the spherical particles can be inhibited, and thus it allows lengthening the long axis of the rod-like particles.

Further, if the amount of the strong reducing agent in the first reduction process is large within the appropriate range and the reduction of the metallic ions progresses such that the amount of the metallic ions in the aqueous metallic salt solution becomes 50% to 1%, the non-reduced amount of the metallic ions is decreased. Therefore, in the second reduction process, the yield of the metallic fine particles can be improved. Also, by changing the kind of the reducing agent, it is possible to adjust the reduction ability. For example, if dimethylamineborane is used, it has stronger reduction ability as compared to that of sodium boron hydride and thus even by a small addition the similar effect can be obtained. Furthermore, if sodium is used, the use of undesired material can be avoided depending on the usage (for example, use for the wiring).

Moreover, by adjusting the amount of the weak reducing agent in the second reduction process, it is possible to control the aspect ratio of the rod-like particles. For example, by increasing the amount of the amine within an appropriate range, in the second reduction process the creation of seed particles by the reduction of the metallic ions is progressed, and thereby at the time of the creation of the seed particles a portion of the metallic ions is exhausted. Therefore, the growth speed of the previously created seed particles is decreased relatively, and then rod-like particles in which the long axis is short relatively can be formed. On the other hand, by decreasing the amount of the amine, the creation amount of the seed particles become small, and then rod-like particles in which the long axis is long relatively can be obtained. Furthermore, if the kind of the amine is changed, similarly to the case in which the reduction abilities are different and the additive amount is increased, it is possible to adjust the shape. In addition, if necessary, in producing the metallic fine particles, various additives can be added.

According to the production process of the present invention, two reduction steps of the metallic ions using two reducing agents which significantly differ in reducing ability thereof, where initially the strong reducing agent is added to the aqueous metallic salt solution and then the weak reducing agent is added to the resultant solution, can be performed in the same vessel. Hence, the operation becomes simple, and large metal nano rods can be produced.

According to the production process of the present invention, metal nano rods in which the long axis is 400 nm or less and the aspect ratio is greater than 1 can be obtained. An absorption wavelength region of the metal nano rods varies by adjusting the aspect ratio. For example, if the metal species is gold, it shows wider particular absorption wavelength from the visible light region (approximately 530 nm) to near-infrared region. Preferably, the long axis of the metal nano rods is less than 200 nm. If the long axis of the metal nano rods is less than 200 nm, the nano rods are not visible as a particles and high transparent material in light of use in filter can be obtained. If the aspect ratio (length of long axis/length of short axis) is 1, only light-absorbing property substantially similar to the spherical metallic fine particles can be obtained (absorptions of approximately 530 nm in gold and approximately 400 nm in silver) and selective absorption effects to any wavelengths of the visible light and near-infrared light can not be obtained.

According to the production process of the present invention, the metal nano rods dispersed in the combined aqueous solution can be obtained. By surface-treating the metal nano rods, they can be stably dispersed in the nonaqueous solvent (solvents other than water). The surface treatment can be performed by dissolving the nitrogen-containing compound and/or the sulfur-containing compound (hereinafter, referred to as "nonaqueous dispersing agent") other than the aforementioned formulas (1) to (5) in the nonaqueous solvent, adding the resultant solution to the aqueous dispersion of the metal nano rods and then absorbing the nonaqueous dispersing agent onto the surface of the metal nano rods. By such surface treatment, the metal nano rods can be extracted in the nonaqueous solvent.

The nitrogen-containing compound used as the nonaqueous dispersing agent is 100 to 10000 and preferably 1000 to 3000 in number average molecular weight. Further, the nitrogen-containing compound includes a dispersing agent in which the main chain thereof has species having high absorption for the metal nano rods (for example, any one of nitrogen, sulfur in the case that the metal is any one of gold, silver and copper) as an absorption site and has a plurality of side chains having affinity for the nonaqueous solvent. If the number average molecular weight is less than 100, dispersion stability in the nonaqueous solvent is insufficient. If the number average molecular weight exceeds 10,000, solubility in the nonaqueous solvent is decreased and also the stability is damaged, and besides, because the dispersing agent itself becomes impurities, the performances of the metal nano rods (for example, electrical property) are degraded.

Such a nonaqueous dispersing agent includes available dispersing agents. For example, such available dispersing agents include Solsperse 13940, Solsperse 24000 SC, Solsperse 28000, Solsperse 32000 (up to here, produced by Avecia Limited.), FLOWLEN DOPA-15 B, FLOWLEN DOPA-17 (up to here, produced by KYOEISHA CHEMICAL Co., LTD), AJISPER PB814, AJISPER-PB711 (up to here, produced by Ajinomoto Fine-Techno. Co. Inc), DisperBYK 160, DisperBYK 161, DisperBYK 162, DisperBYK 163, Disper BYK 183, Disper BYK 184, Disper BYK 185 (up to here, produced by BYK-chemie JAPAN). For example, Solsperse 24000 SC is a so-called "comb-like structure" dispersing agent in which the main chain thereof has a plurality of nitrogens having high absorption for the metal nano rods as an absorption site and side chains have high solubility for the nonaqueous solvent such as aromatic series, ketones and esters. If such a dispersing agent is used, it is possible to disperse the metal nano rods in the nonaqueous solvent with the dispersing agent absorbed in the nitrogen site in the surface of the metal nano rods.

The sulfur-containing compound used as the nonaqueous dispersing agent includes sulfur, or any other species that can be dissolved in the nonaqueous solvent. Specific examples of such a compound include butanethiol, hexanethiol, octanethiol, decanethiol, and dodecanethiol.

The additive amount of the nonaqueous dispersing agent is 0.00001 to 20 parts by weight for 100 parts by weight of the nonaqueous solvent, and preferably 0.0001 to 10 parts by weight. If the additive amount is too high, it is disadvantageous in cost and since the nonaqueous dispersing agent itself serves as impurities, the performance of the metal nano rods is degraded. On the other hand, if the additive amount is too small, because the absorbed amount to the surface of the metal nano rods is small, the dispersion stability in the nonaqueous solvent of the metal nano rods is damaged and then the agglomeration of the metal nano rods occurs easily.

When surface-treated using the nonaqueous dispersing agent, the solution that dissolves or separates the surfactant may be used together with the nonaqueous dispersing agent. Such solutions include a solution that has hydrophilic property and solubility of the surfactant to be absorbed on the surface of the metal nano rods can be increased when mixed with water. Specific examples of the solutions include alcohols such as methanol and ethanol, and ketones such as acetone, ethyl methyl ketone and methyl isobutyl ketone.

For example, if desired that the gold nano rods be extracted from the aqueous dispersing agent of the gold nano rods containing 0.3 parts by weight of the gold nano rods in the nonaqueous solvent, the capacity of the aqueous dispersing agent of the gold nano rods for the nonaqueous solvent be 0.01 to 10 times and preferably 0.1 to 1 times. If the capacity of the aqueous dispersing agent of the gold nano rods is not appropriate, it is difficult to stably extract the metal nano rods into the nonaqueous solvent.

If the surfactant is incorporated into the aqueous dispersing agent of the gold nano rods obtained by the production process of the present invention and the metal nano rods recovered from the solution is used as the conducting materials, high electric conductivity can not be obtained, since the surfactant shows insulation action. Therefore, it is preferable to decrease or eliminate the surfactant after production. In general, as such conducting materials, the amount of the surfactant preferably is 15 parts by weight or less and more preferably 5 parts by weight or less.

Methods of decreasing or eliminating the surfactant include (i) the surface-treatment, (ii) precipitation method by addition of a poor solvent, and (iii) centrifugal separation. According to the surface-treatment, since it is difficult to dissolve the hydrophilic surfactant in the nonaqueous solvent, the surfactant can be decreased or eliminated while the metal nano rods are extracted in the nonaqueous solvent. The precipitation method by addition of a poor solvent is a method in which the metal nano rods are precipitated by adding the solution in which the surfactant is dissolved and is poor solvent with respect to the dispersion solution of the metal nano rods, and then the surfactant remaining in the supernatant is eliminated. The centrifugal separation is a method in which the metal nano rods are precipitated by applying the centrifugal force to the dispersion solution of the metal nano rods and then the surfactant remaining in the supernatant is eliminated. Further, by combining 2 or more of these methods, the surfactant of the metal nano rods can be effectively decreased or eliminated.

For example, most of the surfactant is eliminated by concentrating the metal nano rods in the small amount of toluene by surface-treating using the nitrogen-containing compound having affinity for the nonaqueous solvent of toluene and simultaneously forming a paste of the metal nano rods and toluene. The ethanol as a poor solvent is added to the obtained paste and then the metal nano rods that are covered with a dispersing agent having affinity for the toluene are concentrated. Thereafter, by performing centrifugal separation in order to accelerate the precipitation speed of the concentration, the concentrated material of the metal nano rods is precipitated rapidly. The surfactant can be eliminated by dissolving in ethanol and remaining in an ethanol layer (a portion of toluene) of the supernatant. Subsequently, it is possible to obtain a paste decreased in organic component by re-dispersing the precipitated metal nano rods covered with a dispersing agent having affinity for the toluene by a small amount of toluene.

According to the production process of the present invention, the obtained metal nano rods can be used as the metal nano rod-containing composition by surface-treating it by the nonaqueous dispersing agent and then adding the dispersion media and resins (binders) to the resultant solution. Such resins (binders) may include, but are not limited to, various resins having transparency to the light from visible light widely used as the coating material or the molding material to near-infrared light. Representative examples may include various organic resins such as acryl resin, polyester resin, alkyd resin, urethane resin, silicon resin, fluorine resin, epoxy resin, polycarbonate resin, polyvinyl chloride resin and polyvinyl alcohol, radical polymerizable oligomer or monomer (if necessary, used together with curing agent or radical polymerizable initiator), and sol-gel solution used alkoxysilane as the backbone of the resin.

Preferably, the solvent used in the metal nano rod-containing composition if necessary may include a solvent in which the binder can be stably dissolved or dispersed. Specific examples of such solvents may include, but are not limited to, other than water, alcohol such as methanol, ethanol, propanol, hexanol and ethylene glycol, glycol such as ethylene glycol, aromatic hydrocarbon such as xylene and toluene, alicyclic hydrocarbon such as cyclohexane, ketone such as acetone, methyl ethyl ketone and methyl isobutyl ketone, ester such as acetic ether and butyl acetate, ether such as ethylene glycol monobutyl ether, and the combinations thereof.

The content of the metal nano rods in the metal nano rod-containing composition is 0.01 to 1900 parts by weight with respect to 100 parts by weight of binder. Preferably, if used in optics, the content of the metal nano rods is 0.1 to 50 parts by weight with respect to 100 parts by weight of the binder. Further, preferably, if used in the conducting material, the content of the metal nano rods is 550 to 1900 parts by weight with respect to 100 parts by weight of the binder. If the content of the metal nano rods is below the amount when used in optics, the absorption is small and then desired coloration (mitigation effect of transparency in the case of near-infrared region) can be obtained. On the other hand, if the content of the metal nano rods is greater than the amount, the metal nano rods are concentrated with each other and thereby clear wavelength absorption effect can not be obtained. If the content of the metal nano rods is below the amount when used as the conducting material, the isolation effect of the binder is increased, and then high conductivity can not be obtained. On the other hand, if the content of the metal nano rods is greater than the amount, the metal nano rods are concentrated with each other and thereby preservation stability can be degraded.

The amount of the nonaqueous dispersing agent absorbed on the metal nano rods is 5 to 50 wt %, preferably 8 to 30 wt % with respect to the metal nano rods when used in optics. Other than these ranges, the metal nano rods can be easily concentrated. Furthermore, when the rods are used as the conducting material, the amount of the nonaqueous dispersing agent preferably is 8 to 15 wt %. If the additive amount is above the amount, the conductivity becomes worse.

The metal nano rod-containing composition of the present invention may include the colorant, the pigment, the phosphor, metal oxide, one or more of the metal nano fiber, if necessary. Further, if desired, leveling agents, antifoamers, and other various additives may be added. The metal nano rod may be used in combination with the same or 2 or more different metal nano rods.

By using the metal nano rod-containing composition of the present invention as various types such as coating material compositions, coating films, films, or plates, light absorption material having a layer of filter formed by light absorbing compositions can be obtained. In particular, for example, if the metal nano rod-containing composition is directly coated or printed on the base material, visible light and near-infrared light can be absorbed, and then a cured coating film is formed as a filter for absorbing visible light and near-infrared light. Alternatively, if the composition of the present invention is formed in the forms of films or plate, the composition is deposited or enclosed on the base material such that visible light and near-infrared light are absorbed as a filter. Alternatively, formation in which coating films or films formed by the composition of the present invention are deposited on transparent glass or plastic base materials, and then the layered product is deposited or enclosed on the base material such that visible light and near-infrared light are absorbed as a filter. As per the using forms in the aforementioned cases, the thickness of the light absorbing filter preferably is approximately 0.01 µm to 1 mM, and preferably 0.1 µm to 100 µm in light of the costs or the optical transparency.

Coat films, films, or plates formed by the metal nano rod-containing composition of the present invention as a layer of filter, for example, may be used as a light absorbing material having superior heat resistance such as a visible light and near-infrared light cutting film, a visible light and near-infrared light cutting filter, or a visible light and near-infrared light cutting glass.

The metal nano rods of the present invention have different characteristics depending on the species of the metal, the form of the particles, and aspect ratio. For example, if the species of the metal is gold, the metal nano rods have Plasmon absorption characteristics at a long-wavelength side other than around the 530 nm depending on the aspect ratio, and have high heat resistance, antiweatherability and chemical resistance depending on the gold. Hence, the metal nano rods in which the species of the metal is gold are suitable for materials of optical filters, high-quality coloring agents, near-infrared light absorbers, anticounterfeit inks, biosensors, DNA chips DNA, and surface-enhanced fluorescence sensors. Further, in that gold is a safe material to the living body, the metal nano rods may be used as the materials of food additive coloring agents, coloring agents for cosmetics, living body markers, drug containers for drug delivery system (DDS), test agents, etc. Further, in that gold shows high conductivity, the metal nano rods may be used as wiring materials, electrode materials, electromagnetic shielding materials, etc. Still further, the metal nano rods may be used as polarization materials, recording devices, nano waveguides, etc. based on shape anisotropy of the nano rods. Furthermore, since the surface area formed by particles is large, the metal nano rods may be used as a material that provides the site of catalytic reaction.

EXAMPLES

The present invention will be described in detail with reference to examples and comparative examples herein below. The following examples are directed to gold nano rods. The examples show a light absorbing function mainly at the wavelength of 530 nm to 1242 nm. However, the examples may obtain the same light absorbing function even at the wavelength of 530 nm to 1242 nm or greater, by changing conditions such as the type, length, composition of the metal nano rods. Spectroscopic characterization was measured using V-570 (produced by JASCO Corporation; trademark). Specific resistance value was measured using Loresta GP (produced by Mitsubishi Chemical Corporation; trademark). The condition of producing the metal nano rods is listed in Table 1.

Example A-1

0.2 ml of 10 mM silver nitrate aqueous solution was added to 10 ml of 300 mM hexadecyl trimethyl ammonium bromide (CT16AB). The addition of the silver compound serves to adjust the aspect ratio of the gold nano rods, similarly to the known combining method of the gold nano rods. 0.4 ml of 24 mM gold chloride acid aqueous solution was added to the obtained solution and then was stirred. Subsequently, 10 mM sodium boron hydride was added to the resultant solution used as the strong reducing agent of the first reduction process on six times until the additive amount of the sodium boron hydride became 6 µmol. As sodium boron hydride was added, gold ions were reduced. The color of complex of Gold ions and surfactant in the solution (yellow color, absorption wavelength 394 nm) was weak, and then after 10 minutes, a nearly colorless solution having a weak orange color was obtained.

At this time, the reduced amount of the gold ions was 90%. The value was obtained by adding the strong reducing agent to the separately prepared reaction solution having the same composition in the same condition mentioned in the above, centrifuging (201,000 g) the added solution into precipitate of the gold reduced in an ion valence of 0 and the supernatant gold ions aqueous solution by means of an ultra centrifuge rotor for 10 minutes, and then measuring the content of the supernatant gold ions by means of the inductively-coupled plasma spectrometer.

Subsequently, 200 µmol of triethylamine was added to the resultant solution as the weak reducing agent of the second reduction process, the resultant solution was stirred for 30 seconds, and then was allowed to stand at 30° C. for 48 hours. The amount of the metal ions with the thus obtained aqueous solution was zero. In addition, gold nano rods having the short axis of approximately 8 nm, the long axis of approximately 44 nm, the aspect ratio of approximately 5.5 and absorption at the vicinity of 918 nm were obtained (see FIG. 1).

Example A-2

The aqueous solution was combined in a manner similar to Example A-1, except that 10 mM the potassium borohydride aqueous solution was added as the strong reducing agent of the first reduction process until the additive amount of the potassium borohydride became 6 µmol. The amount of the metal ions with the thus obtained aqueous solution was zero. In addition, gold nano rods having the short axis of approximately 7 nm, the long axis of approximately 34 nm, the aspect ratio of approximately 4.8 and absorption at the vicinity of 870 nm were obtained (see FIG. 1).

Example A-3

The aqueous solution was combined in a manner similar to Example A-1, except that 10 mM the lithium borohydride aqueous solution was added as the strong reducing agent of the first reduction process until the additive amount of the lithium borohydride became 6 µmol. The amount of the metal ions with the thus obtained aqueous solution was zero. In addition, gold nano rods having the short axis of approximately 8 nm, the long axis of approximately 42 nm, the aspect ratio of approximately 5.3 and absorption at the vicinity of 908 nm were obtained (see FIG. 1).

Example A-4

The aqueous solution was combined in a manner similar to Example A-1, except that 10 mM the dimethylamineborane aqueous solution was added as the strong reducing agent of the first reduction process until the additive amount of the dimethylamineborane becomes 2 µmol. The amount of the metal ions with the thus obtained aqueous solution was zero. In addition, gold nano rods having the short axis of approximately 6 nm, the long axis of approximately 52 nm, the aspect ratio of approximately 8.6 and absorption at the vicinity of 962 nm were obtained (see FIG. 1).

Example A-5

The aqueous solution was combined in a manner similar to Example A-1, except that 10 mM the hydrazine aqueous solution was added as the strong reducing agent of the first reduction process until the additive amount of the hydrazine became 1 µmol. The amount of the metal ions with the thus obtained aqueous solution was zero. In addition, gold nano rods having the short axis of approximately 6 nm, the long axis of approximately 29 nm, the aspect ratio of approximately 4.8 and absorption at the vicinity of 864 nm was obtained (see FIG. 1).

Example A-6

The aqueous solution was combined in a manner similar to Example A-1, except that 10 mM the ascorbic acid aqueous solution was added as the strong reducing agent of the first reduction process until the additive amount of the ascorbic acid became 1 µmol. The amount of the metal ions with the thus obtained aqueous solution was zero. In addition, gold nano rods having the short axis of approximately 8 nm, the long axis of approximately 38 nm, the aspect ratio of approximately 4.8 and absorption at the vicinity of 862 nm were obtained (see FIG. 1).

Example A-7

Figure 2:
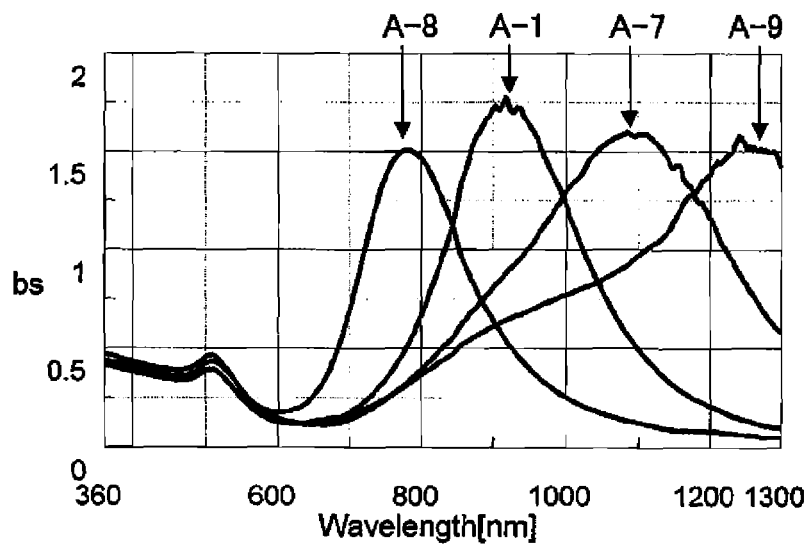
FIG. 2 is a graph illustrating dispersions of the Example A-1, and Example A-7 to Example A-9.

The aqueous solution was combined in a manner similar to Example A-1, except that 100 µmol of the triethylamine was added as the weak reducing agent of the second reduction. The amount of the metal ions with thus obtained aqueous solution was zero. In addition, gold nano rods having the short axis of approximately 9 nm, the long axis of approximately 90 nm, the aspect ratio of approximately 10.0 and absorption at the vicinity of 1084 nm were obtained (see FIG. 2).

Example A-8

The aqueous solution was combined in a manner similar to Example A-1, except that 10 mM the sodium boron hydride aqueous solution was added as the strong reducing agent of the first reduction process until the additive amount of the sodium boron hydride became 3 µmol. The amount of the metal ions with the thus obtained aqueous solution was zero. In addition, gold nano rods having the short axis of approximately 5 nm, the long axis of approximately 19 nm, the aspect ratio of approximately 3.8 and absorption at the vicinity of 780 nm were obtained (see FIG. 2).

Example A-9

The aqueous solution was combined in a manner similar to Example A-1, except that 200 µmol of the tri-n-butyl amine was added as the weak reducing agent of the second reduction. The amount of the metal ions with thus obtained aqueous solution was zero. In addition, gold nano rods having the short axis of approximately 8 nm, the long axis of approximately 102 nm, the aspect ratio of approximately 12.7 and absorption at the vicinity of 1242 nm were obtained (see FIG. 2).

Example A-10

The nitrogen-containing dispersing agent, 1 wt % of Solsperse 24000 SC was dissolved into 2.5 parts by weight of the gold nano rod aqueous dispersion prepared in Example A-1, 1.0 parts by weight of toluene was added to the dissolved solution, and then the resultant solution was stirred for 3 minutes. 5.0 parts by weight of ethanol was added to the resultant mixture, again the solution was stirred for 5 minutes, and then after stirring, was allowed to stand for 24 hours. The mixture was clearly separated into two layers such that the lower layer was a transparent water layer and the upper layer is a toluene layer dispersed by gold nano rods. The upper layer was withdrawn and then the content of gold was measured using ICP. As a result, almost gold nano rods surface-treated by dispersing agent were extracted in the nonaqueous solvent. Further, preservation stability was ascertained and then the dispersion kept stable for 90 days (see Table 2).

Example A-11

The sulfur-containing dispersing agent, 1 wt % of dodecanethiol was dissolved into 2.5 parts by weight of the gold nano rod aqueous dispersion prepared in Example A-1, 1.0 parts by weight of n-hexane was added to the dissolved solution, and then the added resultant solution was stirred for 3 minutes. 5.0 parts by weight of acetone was added to the resultant mixture, again the solution was stirred for 5 minutes, and then after stirring, was allowed to stand for 24 hours. The mixture was clearly separated into two layers such that the lower layer was a transparent water layer and the upper layer was an n-hexane layer dispersed by gold nano rods. The upper layer was withdrawn and then the content of gold was measured using ICP. As a result, almost all gold nano rods surface-treated by dispersing agent were extracted in the nonaqueous solvent. Further, preservation stability was ascertained and then the dispersion kept stable for 90 days (see Table 2).

Example A-12

The gold nano rods combined in a manner of Example A-1 were extracted with toluene in a manner similar to Example A-10. The gold nano rod toluene dispersion liquid was provided to the evaporator, the toluene was removed, and a paste of 5 wt % of toluene was prepared from the gold nano rod. Thereafter, heating residue was measured by Tg-DTA. As a result, the paste contained 25 wt % of an organic component (CT16AB, Solsperse 24000 SC, triethylamine). 10 parts by weight of ethanol which is a poor solvent of Solsperse 24000 SC was added to 10 parts by weight of the paste to agglomerate Solsperse 24000 SC and the gold nano rods. The solution was centrifuged at 40000 g for 30 minutes, agglomeration was precipitated, and then supernatant ethanol solution containing CT16AB and triethylamine was removed. The precipitate was re-dispersed by toluene, and 5 wt % of gold nano rod toluene dispersion liquid was obtained. Thereafter, heating residue was measured by Tg-DTA. As a result, an organic component of the paste was decreased to 0.5 wt %. The obtained gold nano rod toluene paste was coated by bar-coater # 40 and the coated paste was heated at 300° C. for 30 minutes. Thereafter, the specific resistance of the heated coating film was measured, and the measured specific resistance was $5 \times 10^6 \Omega \cdot cm$ (see Table 3).

Example A-13

Figure 4:
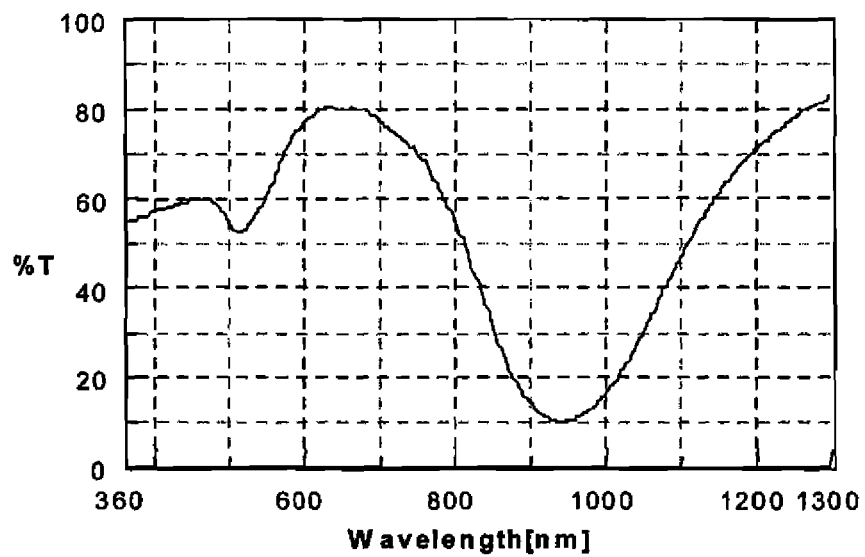
FIG. 4 is a graph illustrating a dispersion of the Example A-13.

Using the gold nano rod paste obtained in Example A-12, the coating material was mixed with the compounding ratio shown in Table 4 and then formed. Gold nano rods, binder and solvent were mixed, and thereby the light absorbing composition was prepared. The coating material was coated over the glass substrates by a spin-coater, the coated substrate was allowed to stand for 5 minutes, thereafter was irradiated and cured by ultraviolet ray by means of high-pressure mercury lamp, and thereby a light absorbing filter was formed. The transmittance was measured with respect to the filter (see Table 4). The measured transmittance in the visible region showed high transmittance of 54%. Furthermore, the transmittance in the vicinity of 950 nm, which is a Plasmon absorption peak of the gold nano rods, was 10% and therefore was shown to be a superior cutting ratio (see FIG. 4).

Comparative Example B-1

Figure 3:
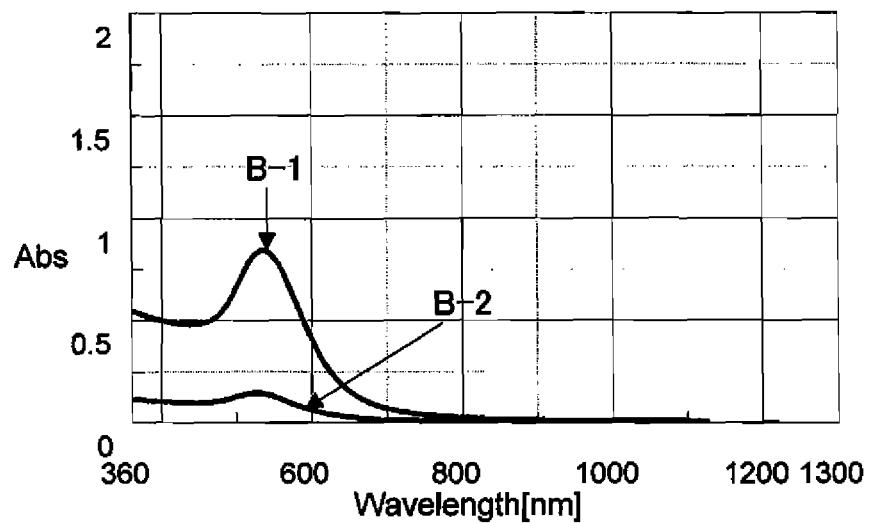
FIG. 3 is a graph illustrating dispersions of the Comparative Examples B-1 and B-2.

The aqueous solution was combined in a manner similar to Example A-1, except that the sodium boron hydride aqueous solution was added as the reducing agent of the second reduction process until the additive amount of the sodium boron hydride became 200 μmol. As a result, spherical gold particles having absorption peak in the vicinity of 538 nm and having approximately 20 nm in diameter were created and gold nano rods were not obtained (see FIG. 3).

Comparative Example B-2

The aqueous solution was combined by reducing the metal ions in a manner similar to Example A-1, except that the weak reducing agent of the second reduction process was not added. As a result, spherical gold particles having absorption peak in the vicinity of 528 nm and having approximately 15 nm in diameter were created and gold nano rods were not obtained (see FIG. 3).

Comparative Example B-3

1.0 parts by weight of toluene was added into 2.5 parts by weight of the gold nano rod aqueous dispersion prepared in Example 1, and then the added resultant solution was stirred for 3 minutes. 5.0 parts by weight of ethanol was added to the resultant mixture, again the solution was stirred for 5 minutes, and then after the termination of stirring, was allowed to stand for 24 hours. As a result, gold nano rod surface-treated by dispersing agent was hardly extracted in the nonaqueous solvent. Further, because CT16AB absorbed on the gold nano rods was separated and dissolved from the surface of the gold nano rods by ethanol, and the gold nano rods were agglomerated to each other, they were precipitated in a clusters and not re-dispersed in the water or nonaqueous solvent (see Table 2).

Comparative Example B-4

The toluene was removed from the gold nano rod toluene dispersion liquid extracted in Example A-10 by the evaporator, and a paste of toluene in which gold nano rods were 5 wt % was prepared. Thereafter, heating residue was measured by Tg-DTA. As a result, the paste contained 25 wt % of an organic component (CT16AB, Solsperse 24000 SC, triethylamine). The obtained gold nano rod toluene paste was coated by bar-coater # 40 and the coated paste was heated at 300° C. for 30 minutes. Thereafter, the specific resistance of the heated coating film was measured, and conductivity was not confirmed (see Table 3).

TABLE 1

Examples of producing the gold nano rods

| | | A-1 | A-2 | A-3 | A-4 | A-5 | A-6 | A-7 | A-8 | A-9 | B-1 | B-2 |
|---|---|---|---|---|---|---|---|---|---|---|---|---|
| Surfactant | 300 mM $CT_{16}AB$ aqueous solution | 10 | 10 | 10 | 10 | 10 | 10 | 10 | 10 | 10 | 10 | 10 |
| Additive | 10 mM silver nitrate aqueous solution | 0.2 | 0.2 | 0.2 | 0.2 | 0.2 | 0.2 | 0.2 | 0.2 | 0.2 | 0.2 | 0.2 |
| Raw material | 24 mM gold chloride acid aqueous solution | 0.4 | 0.4 | 0.4 | 0.4 | 0.4 | 0.4 | 0.4 | 0.4 | 0.4 | 0.4 | 0.4 |
| Reductants of the first reduction process | 10 mM $NaBH_4$ (6 µmol) | 0.6 | | | | | | | | | 0.6 | 0.6 |
| | 10 mM $KBH_4$ (6 µmol) | | 0.6 | | | | | | | | | |
| | 10 mM $LiBH_4$ (6 µmol) | | | 0.6 | | | | | | | | |
| | 10 mM $BH_3 \cdot NH(CH_3)_2$ (2 µmol) | | | | 0.2 | | | | | | | |
| | 10 mM hydrazine (1 µmol) | | | | | 0.1 | | | | | | |
| | 10 mM ascorbic acid (1 µmol) | | | | | | 0.1 | | | | | |
| | 10 mM $NaBH_4$ (6 µmol) | | | | | | | 0.6 | | | | |
| | 10 mM $NaBH_4$ (3 µmol) | | | | | | | | 0.3 | | | |
| | 10 mM $NaBH_4$ (6 µmol) | | | | | | | | | 0.6 | | |
| Reductants of the second reduction process | Triethylamine | 0.028 | 0.028 | 0.028 | 0.028 | 0.028 | 0.028 | 0.014 | 0.028 | | | |
| | tri-n-butylamine | | | | | | | | | 0.048 | | |
| | 10 mM $NaBH_4$ (200 µmol) | | | | | | | | | | 20 | |
| Characteristic | length of long axis [nm] | 8 | 7 | 8 | 6 | 6 | 8 | 9 | 5 | 8 | 20 | 15 |
| | length of short axis [nm] | 44 | 34 | 42 | 52 | 29 | 38 | 90 | 19 | 102 | | |
| | Aspect ratio | 5.5 | 4.8 | 5.3 | 8.6 | 4.8 | 4.8 | 10 | 3.8 | 12.7 | | |
| | Peak of absorption wavelength [nm] | 918 | 870 | 908 | 962 | 864 | 862 | 1084 | 780 | 1242 | 538 | 528 |

(Note 1) A-1 to A9 are Examples, B-1 to B-2 are Comparative Examples, and ml is the unit of additive amount.
(Note 2) in the second reduction process, 0.028 ml of triethylamine is 200 µmol, 0.014 ml of triethylamine is 100 µmol, and 0.048 ml of tri-n-butylamine is 200 µmol

TABLE 2

Surface treatment extraction operation [part by weight]

| | | Example A-10 | Example A-11 | Comparative Example B-3 |
|---|---|---|---|---|
| Gold nano rod aqueous dispersion | 0.03 wt % containing | 2.5 | 2.5 | 2.5 |
| Nitrogen-containing dispersing agent | Solsperse 24000SC | 0.01 | | |
| Thiol radical-containing dispersing agent | dodecanethiol | | 0.01 | |
| Nonaqueous solvent | toluene | 1 | | 1 |
| | n-hexane | | 1 | |
| Aqueous dispersing agent dissolution | ethanol | 5 | | 5 |
| | Acetone | | 5 | |
| Extraction ratio of gold nano rods [%] | Aqueous | 1 | 1 | 99 |
| | Nonaqueous | 99 | 99 | 1 |
| dispersion stability in the nonaqueous solvent | *1 | 90 days or more | 90 days or more | aggregation |

*1 the number of days it takes until precipitation and aggregation are confirmed

TABLE 3

Comparison of conductivity

| | | Example A-12 | Comparative Example B-4 |
|---|---|---|---|
| Metal nano rod | Length of short axis | 8 | 8 |
| | Length of long axis | 44 | 44 |
| | Aspect ratio | 5.5 | 5.5 |
| Refining method of the paste | | Agglomeration method & centrifugal separation method | None |
| Organic component in the paste | | 0.5 wt % | 25.0 wt % |
| specific resistance value [Ω · cm] | | $5 \times 10^{-6}$ | No conductivity |

TABLE 4

Filter for optics [part by weight]

| | | Example A-13 |
|---|---|---|
| binder | Acryl UV curing resin | 100 |
| photopolymerization initiator | α-hydroxyketone | 3 |
| Metal nano rod | Gold nano rod paste | 40 |
| solvent | toluene | 60 |
| transmittance[%] | 940 nm | 10 |
| | 512 nm | 54 |

(Note)
content of gold nano rods: 2 wt %, film thickness: 6 µm

INDUSTRIAL APPLICABILITY

The present invention is applicable to a process for producing a metallic fine particles by chemically reducing metallic ions, the metallic fine particles obtained in accordance with the production process, a composition containing thereof, and the use thereof.

The invention claimed is:

1. A process for producing nano-sized metallic fine particles by chemically reducing metallic ions, wherein the reduction of the metallic ions is performed in 2 steps using two types of reducing agents which significantly differ in reducing ability thereof, a reducing agent in which the reduction ability is strong, referred to as "strong reducing agent", is used in the first reduction step, and a reducing agent in which the reduction ability is weak, referred to as "weak reducing agent", is used in the second reduction step, wherein in the first reduction process, the strong reducing agent is added to an aqueous metallic salt solution, and the reduction is preformed until the amount of metal ions in the aqueous metallic salt solution is 50 to 1%, and subsequently, wherein in the second reduction process, the weak reducing agent is added to an aqueous metallic salt solution, and the reduction is preformed until the amount of metal ions in the aqueous metallic salt solution is substantially 0%, and wherein as the strong reducing agent of the first reduction process, at least one selected from the group consisting of boron hydride, dimethylamine borane, hydrazine, and ascorbic acid is used and wherein as the weak reducing agent of the second reduction process, at least one of alkylamine and alkanolamine is used, which is represented by the following formulas (1) to (4):

$$H_2NR\ (R:C_nH_{2n+1},\ n=\text{integer of 1 to 8}) \quad \text{formula (1)}$$

$$HNR_2\ (R:C_nH_{2n+1},\ n=\text{integer of 1 to 8}) \quad \text{formula (2)}$$

$$NR3:(R:C_nH_{2n+1},\ n=\text{integer of 1 to 8}) \quad \text{formula (3)}$$

$$N(ROH)_3\ (R:C_nH_{2n},\ n=\text{integer of 1 to 8}) \quad \text{formula (4).}$$

2. The process according to claim 1, wherein an aqueous metallic salt solution containing a surfactant, and two reducing agents which significantly differ in reducing ability thereof, are used, metallic ions in an aqueous metallic solution are reduced by adding the strong reducing agent to the aqueous metallic salt solution and subsequently adding the weak reducing agent to the solution, in the same vessel, and thereby nano-sized rod-like metallic fine particles, referred to as "metal nano rods", are produced.

3. The process according to claim 1, wherein the reducing agent that has a weak reducing ability and is used in the second reduction process is triethylamine.

4. The process according to claim 1, wherein the concentration of amines represented by the formulas (1) to (4) present in the aqueous metallic salt solution is in the range of 0.0001 to 10 mol/L.

5. The process according to claim 2, wherein the surfactant is an ammonium salt which substantially has no reducing ability and can be represented by the following formula (5):

$$CH_3(CH_2)_nN^+(CH_3)_3Br^-\ (n=\text{integer of 1 to 17}) \quad \text{formula (5).}$$

6. The process according to claim 2, wherein the concentration of an ammonium salt represented by the formula (5) present in the aqueous metallic salt solution is in the range of 0.01 to 2.0 mol/L.

7. The process according to claim 1, wherein the size of metallic fine particles is controlled by adjusting the additive amount of the strong reducing agent used in the first reduction process and the additive amount of the weak reducing agent used in the second reduction process.

* * * * *